United States Patent
Zhong (10) Patent No.: US 8,594,172 B2
(45) Date of Patent: Nov. 26, 2013

(54) ADAPTATION OF BASELINE WANDER CORRECTION LOOP GAIN SETTINGS

(75) Inventor: Lizhi Zhong, Sunnyvale, CA (US)

(73) Assignee: LSI Corporation, San Jose, CA (US)

( * ) Notice: Subject to any disclaimer, the term of this patent is extended or adjusted under 35 U.S.C. 154(b) by 332 days.

(21) Appl. No.: 12/974,678

(22) Filed: Dec. 21, 2010

(65) Prior Publication Data

US 2012/0155528 A1   Jun. 21, 2012

(51) Int. Cl.
*H04L 27/01* (2006.01)
(52) U.S. Cl.
USPC .......................................... 375/232; 375/345
(58) Field of Classification Search
USPC ......... 375/350, 345, 346, 316, 317, 232, 233; 370/290, 291, 292
See application file for complete search history.

(56) References Cited

U.S. PATENT DOCUMENTS

| | | | |
|---|---|---|---|
| 6,556,635 B1 * | 4/2003 | Dehghan ................... | 375/345 |
| 6,614,842 B1 * | 9/2003 | Chou et al. ................ | 375/232 |
| 7,738,567 B2 | 6/2010 | Miller et al. .............. | 375/258 |
| 2002/0064242 A1 * | 5/2002 | Mita et al. ................. | 375/341 |
| 2003/0142659 A1 * | 7/2003 | Lin et al. ................... | 370/351 |
| 2007/0104300 A1 * | 5/2007 | Esumi et al. .............. | 375/346 |
| 2007/0286315 A1 * | 12/2007 | Hong et al. ................ | 375/345 |
| 2008/0063091 A1 * | 3/2008 | Dong et al. ................ | 375/257 |
| 2008/0159415 A1 * | 7/2008 | Miller et al. .............. | 375/258 |
| 2008/0212715 A1 * | 9/2008 | Chang ....................... | 375/317 |

* cited by examiner

*Primary Examiner* — Aristocratis Fotakis
(74) *Attorney, Agent, or Firm* — Christopher P. Maiorana, PC (57) ABSTRACT

An apparatus including a first circuit and a second circuit. The first circuit may be configured to receive a signal, where low frequency content of the signal is attenuated due to high pass filtering by a medium carrying the signal and a coupling. The second circuit may be configured to automatically set a gain of a baseline wander correction loop to restore the low frequency content in the signal based upon a sample taken from a first point in a signal pathway of the first circuit.

18 Claims, 10 Drawing Sheets

ADAPTATION OF BASELINE WANDER CORRECTION LOOP GAIN SETTINGS

FIELD OF THE INVENTION

The present invention relates to data communications generally and, more particularly, to a method and/or apparatus for adaptation of baseline wander correction loop gain settings.

BACKGROUND OF THE INVENTION

In AC (alternating current) coupled systems, an AC coupling (i.e., capacitive coupling) or an inductive coupling (i.e., transformer coupling) behaves as a high pass filter, only allowing high frequency content to go through. The high pass filter behavior becomes a problem when the data traffic is not DC (direct current) balanced, meaning the traffic has a significant amount of low frequency content. For example, 16 G Fibre Channel (FC) uses 64b/66b coding, which is not DC balanced. The low frequency content is filtered out by the high pass filter behavior of the capacitive or inductive coupling. Baseline wander correction (BLWC) is used to address this problem.

Baseline wander also occurs in medical equipment where the low frequency loss can be due to poor contact. With respect to an electrocardiogram (ECG), the baseline wander is an extraneous, low-frequency activity, which may interfere with signal analysis, making the clinical interpretation inaccurate. When baseline wander takes place, ECG measurements related to the isoelectric line cannot be computed since the isoelectric line is not well-defined. Baseline wander in ECGs is often exercise-induced, and can come from a variety of sources, including perspiration, respiration, body movements and poor electrode contact. The spectral content of the baseline wander in an ECG is usually in the range between 0.05-1 Hz. However, during strenuous exercise, the baseline wander may contain higher frequencies.

A technique for correcting baseline wander is to low pass filter a received signal to restore the low frequency content and add the filtered signal back to the received signal. However, setting a gain for the baseline wander correction is not trivial. The optimal gain setting depends not only on the channel loss in the low frequency region, but also on the de-emphasis settings at the transmitter.

Conventional BLWC techniques involve manually setting the gain. Users either (i) set the gain based on a formula, (ii) sweep across a range of gain settings and pick one that works best, or (iii) find a starting point for the gain using an average of an eye envelope at the receiver input. Setting the gain manually is a significant problem for users, no matter what method is used. The optimal gain depends on the channel loss at the low frequency region, as well as the transmitter (TX) de-emphasis settings. Consequently, the gain needs to be different for different channels and needs to be updated when the TX de-emphasis changes.

It would be desirable to have an automatic adaptation of baseline wander correction loop gain settings.

SUMMARY OF THE INVENTION

The present invention concerns an apparatus including a first circuit and a second circuit. The first circuit may be configured to receive a signal, where low frequency content of the signal is attenuated due to high pass filtering by a medium carrying the signal and a coupling. The second circuit may be configured to automatically set a gain of a baseline wander correction loop to restore the low frequency content in the signal based upon a sample taken from a first point in a signal pathway of the first circuit.

The objects, features and advantages of the present invention include providing a method and/or apparatus for adaptation of baseline wander correction loop gain settings that may (i) automatically find an optimal gain setting for baseline wander correction, (ii) have a simple implementation, (iii) be implemented without any changes to the analog domain, (iv) be implemented by adding an accumulator and gain loop adaptation to the digital domain, (v) have low implementation cost, and/or (vi) use approximations to simplify the adaptation process.

BRIEF DESCRIPTION OF THE DRAWINGS

These and other objects, features and advantages of the present invention will be apparent from the following detailed description and the appended claims and drawings in which:

DETAILED DESCRIPTION OF THE PREFERRED EMBODIMENTS

In one aspect, an example embodiment of the present invention generally provides an adaptation process that may automatically set a baseline wander correction loop gain to minimize mean squared error (MSE) at an input of a detector (e.g., slicer, etc.). Adaptation of baseline wander correction loop gain settings in accordance with the present invention generally uses an error signal, as well as an output signal of a baseline wander correction circuit. The error signal is generally defined similarly to other adaptation techniques. In another aspect, the present invention generally provides a simple way to implement the baseline wander correction gain adaptation process. In one example, an accumulator may be employed in place of an ideal low pass filter to generate the output signal. The approximation made by the use of an accumulator instead of an ideal low pass filter may greatly reduce implementation cost, while not significantly sacrificing performance.

Figure 1:
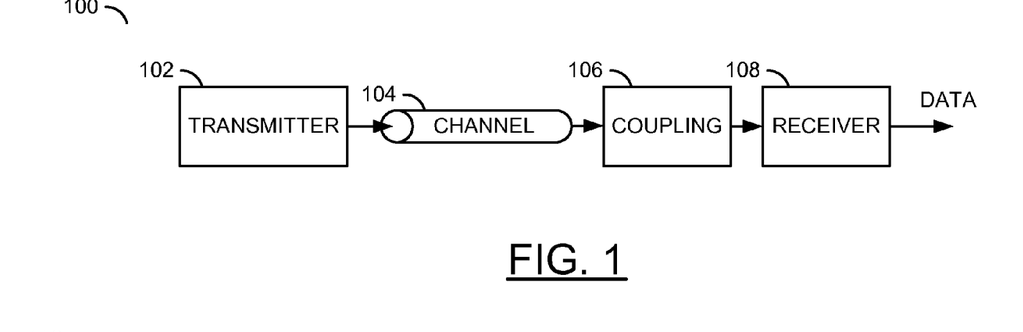
FIG. 1 is a block diagram illustrating a context for baseline wander correction in accordance with the present invention.

Referring to FIG. 1, a block diagram of a circuit 100 is shown illustrating an apparatus including baseline wander correction in accordance with an example embodiment of the present invention. The circuit 100 may include a block (or circuit) 102, a block (or circuit) 104, a block (or circuit) 106, and a block (or circuit) 108. The circuits 102-108 may represent modules and/or blocks that may be implemented as hardware, software, a combination of hardware and software, or other implementation. The circuit 102 may implement, in one example, a transmitter. The circuit 104 may implement, in one example, a channel (e.g., a transmission medium such as air, wire, optical fibre, etc.). The circuit 106 may implement, in one example, a coupling to the transmission medium 104 (e.g., a capacitive coupling, an inductive coupling, an electrode, or other connection). The circuit 106 may be placed between the circuit 104 and either of the circuits 102 and 108. The circuit 108 may implement, in one example, a receiver (e.g., ethernet receiver, medical instrumentation, wireless receiver, etc.).

The circuit 102 may generate a signal carrying data to be communicated to a device connected to an output of the circuit 108. The signal may be communicated to the circuit 108 via the circuit 104 and the circuit 106. The circuit 106 may attenuate low frequency content of the signal, while passing high frequency content. In general, the circuit 106 may behave as a high pass filter.

Figure 2:
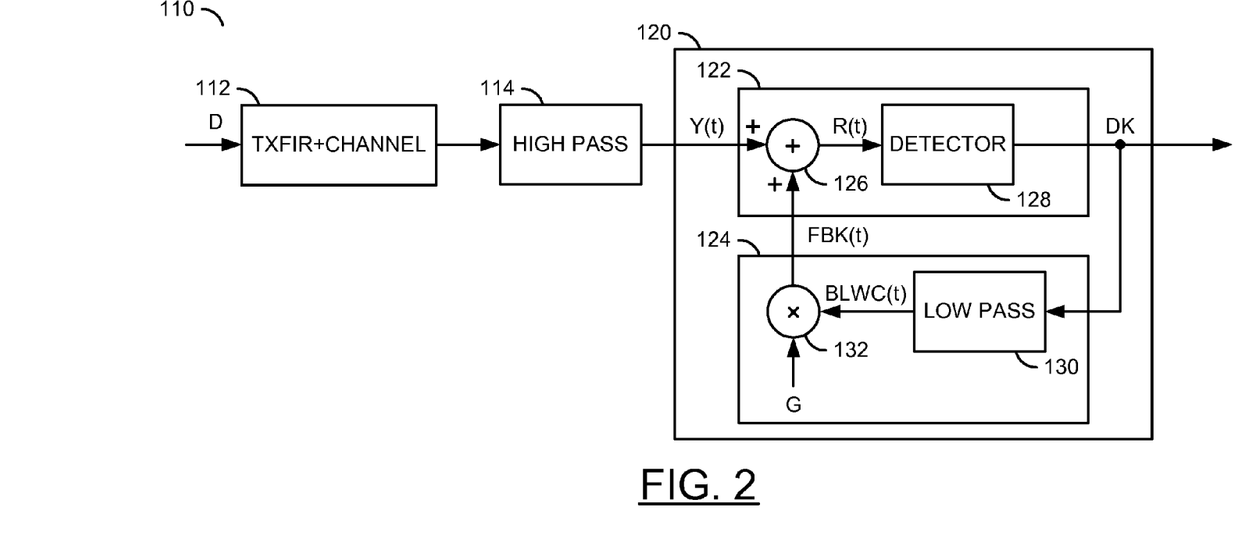
FIG. 2 is a diagram illustrating an example implementation of a baseline wander correction loop in accordance with an example embodiment of the present invention.

Referring to FIG. 2, a diagram is shown illustrating an example circuit 110 implementing baseline wander correction in accordance with an example embodiment of the present invention. In one example, the circuit 110 may comprise a block (or circuit) 112, a block (or circuit) 114, and a block (or circuit) 120. The circuit 112 may represent aggregated transfer characteristics of the circuit 102 and the circuit 104 of FIG. 1. The circuit 114 may implement a high pass filter generally representing the frequency response of the circuit 106 of FIG. 1. The circuit 120 may be used to implement the receiver 108 of FIG. 1.

The circuit 120 may comprise, in one example, a first block (or circuit) 122 and a block (or circuit) 124. The circuit 122 may implement, in one example, a receiver chain (or signal path). The circuit 124 may implement, for example, a baseline wander correction circuit in accordance with an example embodiment of the present invention.

In one example, the circuit 122 may have a first input that may receive a signal (e.g., Y(t)), a second input that may receive a signal (e.g., FBK(t)), and an output that may present a signal (e.g., DK). The signal FBK(t) may comprise a feedback signal containing low frequency content to be restored to the signal Y(t). The signal DK may comprise a recovered data signal. The circuit 122 may be configured to generate the signal DK in response to the signal Y(t) and the signal FBK(t). The circuit 124 may have an input that may receive the signal DK and an output that may present the signal FBK(t).

In one example, the signals Y(t) and FBK(t) may comprise analog signals and the signal DK may comprise a digital signal. In general, signals that are in the analog domain are generally denoted herein as functions of time (e.g., func(t)). Signals in the digital domain are generally denoted without the parenthetical or have a label ending in K (e.g., DK). The suffix K generally denotes the signal as being the Kth sample, symbol, etc.

In one example, the circuit 122 may comprise a block (or circuit) 126 and a block (or circuit) 128. The circuit 126 may implement a summing node. The circuit 128 may implement a detector. The circuit 126 may be implemented, in one example, as an adder. The circuit 128 may be implemented, for example, as a symbol detector, a slicer, or other data detection circuit. The circuit 126 may have a first input that may receive the signal Y(t), a second input that may receive the signal FBK(t), and an output that may present a signal (e.g., R(t)). The signal R(t) generally represents the received signal with low frequency content restored. The circuit 128 may have an input that may receive the signal R(t) and an output that may present the signal DK. The circuit 128 may be configured to generate the signal DK in response to the signal R(t).

In one example, the circuit 124 a block (or circuit) 130 and a block (or circuit) 132. The circuit 130 may comprise a low pass filter. The circuit 132 may be implemented as multiplier. The circuit 130 may have an input that may receive the signal DK and an output that may present a signal (e.g., BLWC(t)). The signal BLWC(t) may implement a baseline wander correction signal. The circuit 132 may have a first input that may receive the signal BLWC(t), a second input that may receive a signal (e.g., G), and an output that may present the signal FBK(t). The signal G may implement a baseline wander correction loop gain. In one example, the baseline wander correction loop gain G may be implemented as a predefined constant. In another example, the baseline wander correction loop gain G may be automatically adapted through an adaptation loop in accordance with an embodiment of the present invention. The circuit 132 is generally configured to apply the gain G to the signal BLWC(t) to generate the signal FBK(t).

The coupling 106 generally behaves as a high pass filter. Non DC balanced traffic (e.g., 16 G fibre channel (FC) using 64b/66b coding) has significant low frequency content which is filtered out by the high pass behavior of the coupling 106. The baseline wander correction provided by the circuit 120 generally restores the low frequency content based upon low pass filtering recovered data (e.g., DK) and adding the filtered data back to the received signal at a point after the coupling 106.

For example, the circuit 128 may recover the data DK from the signal R(t). The recovered data DK may be presented to an input of the circuit 130. The circuit 130 may generate the signal BLWC(t) in response to the signal DK. An output of the circuit 130 may present the signal BLWC(t) to a first input of the circuit 132. The circuit 132 may have a second input that may receive the gain signal G and an output that may present a product of the gain signal G and the signal BLWC(t) as the signal FBK(t), to the second input of the circuit 126. The first input of the circuit 126 may receive the signal Y(t) from the coupling 106 and the output may present the signal R(t) to the input of the circuit 128.

The circuit 124 generally represents a baseline wander correction loop in accordance with an example embodiment of the present invention. In one example, the block 112 may be represented by a transfer function Htx(f)*Hch(f), the block 114 may be represented by a transfer function Hhp(f), and the circuit 130 may be represented by a transfer function Hlp(f).

Operation of the circuit 110 with an optimal gain value may be expressed by the following equation:

$$Sd(f)*|Htx(f)|^{*2}|Hch(f)|^2*|Hhp(f)|^2+Sdk(f)*|Hlp(f)|^2*G^2=Sd(f)*|Htx(f)|^2*|Hch(f)|^2.$$

Figure 3:
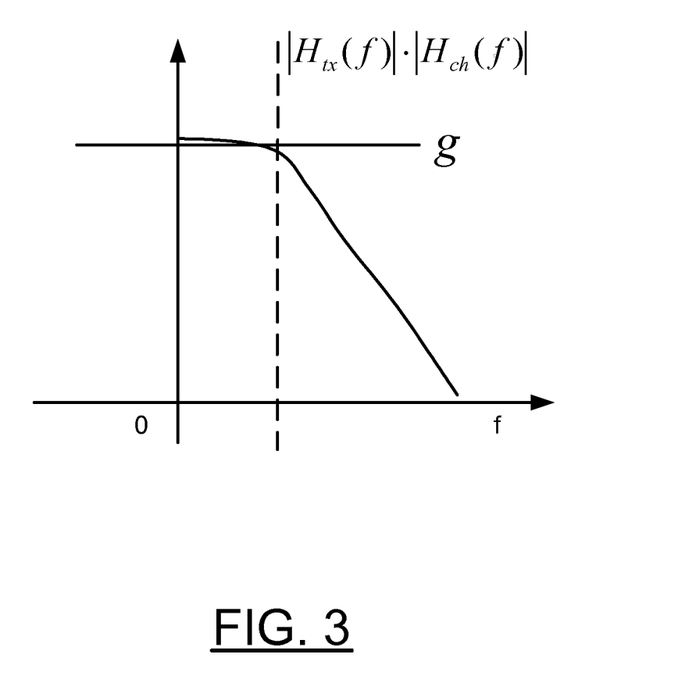
FIG. 3 is a graph illustrating a corner frequency of a low pass filter of FIG. 2.

An expression for the optimal gain value may be obtained by considering Sdk(f) to equal Sd(f) and |Hhp(f)|^2+|Hlp(f)|^2 to be equal to 1. In order to obtain G*|Hlp(f)|=|Htx(f)|*|Hch(f)|*|Hlp(f)|, G may be set to equal |Htx(f)|*|Hch(f)|. A corner frequency of a low pass filter (e.g., see FIG. 3) with G =|Htx(f)|*|Hch(f)|*|Hlp(f)| is generally a sufficient condition for the equation to be true. In one example, G may be set to constant value to simplify implementation of the filter. The constant may be expressed as |Htx(f0)|*|Hch(f0)|, where f0 is a constant that is less than the corner frequency of the low pass filter. In one example, f0 may be set to zero. Based upon the close form expression of the optimal baseline wander correction loop gain, the optimal gain generally depends on transmitter de-emphasis and channel loss within the pass band of the low pass filter implemented in the circuit 130.

Figure 4:
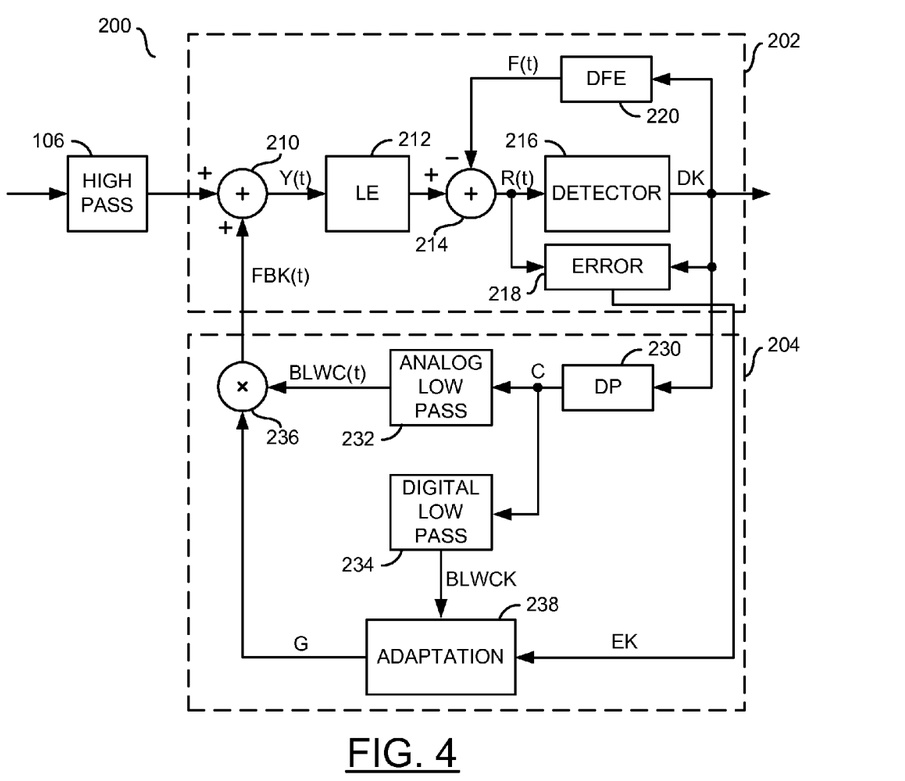
FIG. 4 is a block diagram illustrating an example circuit implementing baseline wander correction loop gain adaptation in accordance with an example embodiment of the present invention.

Referring to FIG. 4, a block diagram of a circuit 200 is shown illustrating another example implementation of baseline wander correction gain adaptation in accordance with another example embodiment of the present invention. In one example, the circuit 200 may comprise a block (or circuit) 202 and a block or circuit 204. The circuit 202 may be implemented, in one example, as a data recovery circuit. The circuit 204 may be implemented, in one example, as a baseline wander correction circuit. The circuit 202 may have a first input that may receive the signal from the coupling 106, a second input that may receive a signal (e.g., FBK(t)), a first output that may present a signal (e.g., DR), and a second output that may present a signal (e.g., EK). The signal DK may comprise recovered data. The signal EK may comprise and error signal. The signal FBK(t) may comprise low frequency content to be restored to the received signal from the coupling 106. The circuit 204 may have a first input that may receive the signal DK, a second input that may receive the signal EK, and an output that may present the signal FBK(t).

The circuit 202 may comprise a block (or circuit) 210, a block (or circuit) 212, a block (or circuit) 214, a block (or circuit) 216, a block (or circuit) 218, and a block (or circuit) 220. The circuit 210 may be implemented, in one example, as an adder. The circuit 212 may be implemented, in one example, as a linear equalizer. The circuit 214 may be implemented, in one example, as an adder. The circuit 216 may be implemented, in one example, as a symbol detector, slicer, or other data detection circuit. The circuit 218 may be implemented, in one example, as an error signal generator. The circuit 220 may implement a decision feedback equalizer (DFE). The circuits 210-220 may be implemented using conventional techniques.

The circuit 210 may have a first input that may receive the signal from the coupling 106, a second input that may receive the signal FBK(t), and an output that may present a signal (e.g., (Y(t)). The signal Y(t) may comprise a sum of the signal from the coupling 106 and the signal FBK(t). The signal Y(t) may be presented to an input of the circuit 212. The circuit 212 may have an output that may present a signal to a first input of the circuit 214. The circuit 214 may have a second input that may receive a signal (e.g., F(t)), and an output that may present a signal (e.g., R(t)). The signal R(t) may comprise, in one example, a difference between the output of the circuit 212 and the signal F(t). The circuit 216 may have an input that may receive the signal R(t) and an output that may present the signal DK. The circuit 218 may have a first input that may receive the signal R(t), a second input that may receive the signal DK, and an output that may present the signal EK. The circuit 220 may have an input that may receive the signal DK and an output that may present the signal F(t). In one example, the circuit 220 may also receive the signal EK.

The circuit 204 may comprise a block (or circuit) 230, a block (or circuit) 232, a block (or circuit) 234, a block (or circuit) 236, and a block (or circuit) 238. The circuit 230 may implement an optional data processing (DP) circuit. The circuit 232 may be implemented, in one example, as an analog low pass filter. The circuit 234 may be implemented, in one example, as a digital low pass filter. The circuit 236 may be implemented, in one example, as a multiplier. The circuit 238 may implement a gain adaptation loop in accordance with an embodiment of the present invention. The circuit 230, when implemented, generally processes the signal DK for use in controlling the circuits 232 and 234. The circuit 230 may be omitted depending upon the particular implementations of the circuits 232 and 234. When the circuit 230 is not implemented, the signal DK may be presented directly to the circuits 222 and 224.

The circuit 230 may have an input that may receive the signal DK and an output that may present a signal (e.g., C) to an input of the circuit 232 and an input of the circuit 234. The circuit 232 may have an output that may present a signal (e.g., BLWC(t)) to a first input of the circuit 236. The signal BLWC(t) may comprise low frequency content to be restored to the received signal. The circuit 234 may have an output that may present a signal (e.g., BLWCK) to a first input of the circuit 238. The circuit 238 may have a second input that may receive the signal EK and an output that may present a signal (e.g., G) to a second input of the circuit 236. The signal G may comprise a loop gain value to be applied to the low frequency content to be restored. The circuit 234 generally has a frequency response that matches a frequency response of the circuit 232. The circuits 234 and 238 generally provide an adaptation loop for determining the appropriate gain value. The circuit 238 may implement the loop gain adaptation using a least mean squares (LMS) technique. The circuit 236 may have an output that may present the signal FBK(t). The signal FBK(t) generally comprises a product of the signal BLWC(t) and the signal G.

Figure 5:
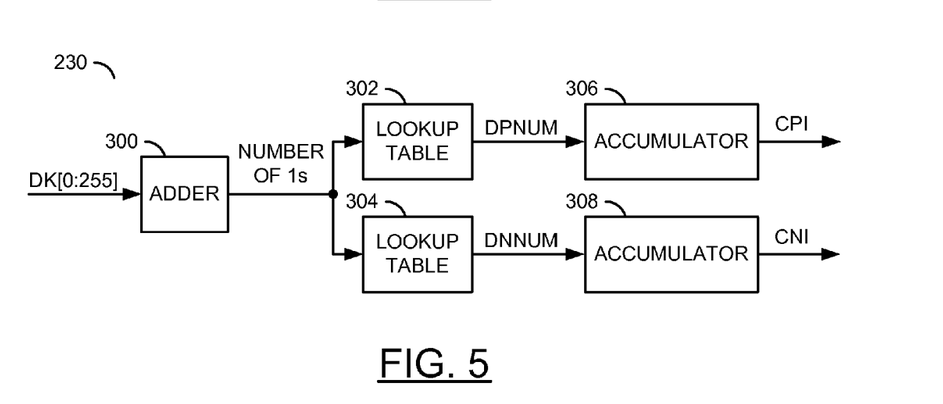
FIG. 5 is a block diagram illustrating an optional data processing block in accordance with an example embodiment of the present invention.

Referring to FIG. 5, a block diagram is shown illustrating an example implementation of the optional data processing block 220 of FIG. 4. In one example, the data processing block 220 may comprise a block (or circuit) 300, a block (or circuit) 302, a block (or circuit) 304, a block (or circuit) 306, and a block (or circuit) 308. The block 300 may be implemented, in one example, as an adder. The block 302 may be implemented, in one example, as a first lookup table. The block 304 may be implemented, in one example, as a second lookup table. The block 306 may be implemented, in one example, as a first accumulator. The block 308 may be implemented, in one example, as a second accumulator.

The block 300 may receive the data signal DK. In one example, the block 300 may be configured to sum a number (e.g., 306) of samples (e.g., DK[0:255]) of the signal DK. However, other number of samples may be implemented accordingly to meet the design criteria of a particular implementation. The block 300 may be configured to present a signal representing the number of ones in the summed data samples to an input of the block 302 and an input of the block 304. The block 302 may be configured to present a signal (e.g., DPNUM) in response to the signal from the block 300. The block 304 may be configured to present a signal (e.g., DNNUM) in response to the signal from the block 300. The signal DPNUM may be presented to an input of the block 306.

The signal DNNUM may be presented to an input of the block 308. The block 306 may present a signal (e.g., CPI) in response to the signal DPNUM. The block 308 may present a signal (e.g., CNI) in response to the signal DNNUM. The signals CPI and CNI generally represent components of the signal C. The signals CPI and CNI may be used to control the circuits 232 and 234.

Figure 6:
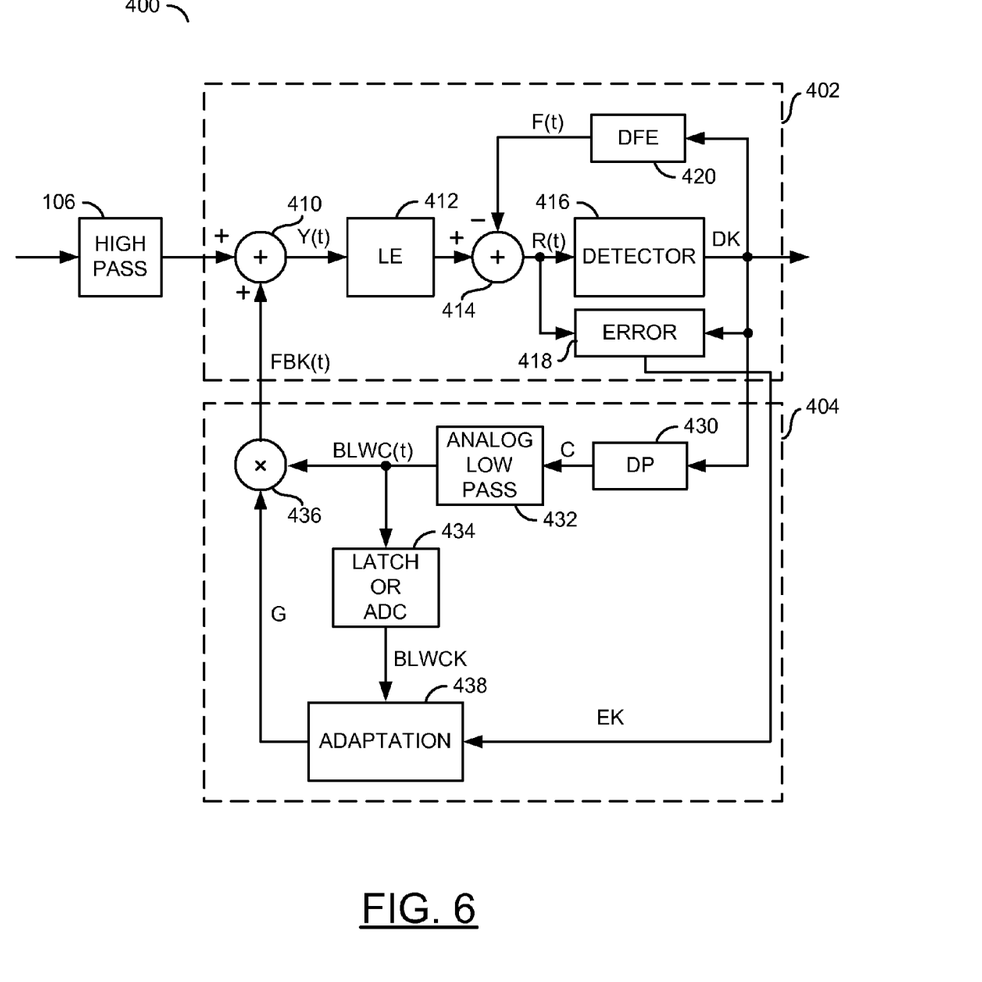
FIG. 6 is a block diagram illustrating another example circuit implementing baseline wander correction loop gain adaptation in accordance with another example embodiment of the present invention.

Referring to FIG. 6, a block diagram of a circuit 400 is shown illustrating another example implementation of baseline wander correction with gain adaptation in accordance with another example embodiment of the present invention. In one example, the circuit 400 may comprise a block (or circuit) 402 and a block or circuit 404. The circuit 402 may be implemented, in one example, as a data recovery circuit. The circuit 404 may be implemented, in one example, as a baseline wander correction circuit. The circuit 402 may have a first input that may receive the signal from the coupling 106, a second input that may receive a signal (e.g., FBK(t)), a first output that may present a signal (e.g., DK), and a second output that may present a signal (e.g., EK). The signal DK may comprise recovered data. The signal EK may comprise an error signal. The signal FBK(t) may comprise low frequency content to be restored to the received signal from the coupling 106. The circuit 404 may have a first input that may receive the signal DK, a second input that may receive the signal EK, and an output that may present the signal FBK(t).

The circuit 402 may comprise a block (or circuit) 410, a block (or circuit) 412, a block (or circuit) 414, a block (or circuit) 416, a block (or circuit) 418, and a block (or circuit) 420. The circuit 410 may be implemented, in one example, as an adder. The circuit 412 may be implemented, in one example, as a linear equalizer. The circuit 414 may be implemented, in one example, as an adder. The circuit 416 may be implemented, in one example, as a symbol detector, slicer, or other data detection circuit. The circuit 418 may be implemented, in one example, as an error signal generator. The circuit 420 may implement a decision feedback equalizer (DFE). The circuits 410-420 may be implemented using conventional techniques.

The circuit 410 may have a first input that may receive the signal from the coupling 106, a second input that may receive the signal FBK(t), and an output that may present a signal (e.g., (Y(t)). The signal Y(t) may comprise a sum of the signal from the coupling 106 and the signal FBK(t). The signal Y(t) may be presented to an input of the circuit 412. The circuit 412 may have an output that may present a signal to a first input of the circuit 414. The circuit 414 may have a second input that may receive a signal (e.g., F(t)) and an output that may present a signal (e.g., R(t)). The signal R(t) may comprise, in one example, a difference between the output of the circuit 412 and the signal F(t). The circuit 416 may have an input that may receive the signal R(t) and an output that may present the signal DK. The circuit 418 may have a first input that may receive the signal R(t), a second input that may receive the signal DK, and an output that may present a signal (e.g., EK). The signal EK may implement an error signal. The circuit 420 may have an input that may receive the signal DK and an output that may present the signal F(t). In one example, the circuit 420 may also receive the signal EK.

The circuit 404 may comprise a block (or circuit) 430, a block (or circuit) 432, a block (or circuit) 434, a block (or circuit) 436, and a block (or circuit) 438. The circuit 430 may implement an optional data processing (DP) circuit. The circuit 432 may be implemented, in one example, as an analog low pass filter. The circuit 434 may be implemented, in one example, as a latch or analog-to-digital convertor (ADC). The circuit 436 may be implemented, in one example, as a multi-plier. In one example, the circuit 438 may implement a gain adaptation loop in accordance with an embodiment of the present invention. The circuit 430, when implemented, generally processes the signal. DK for use in controlling the circuit 432. The circuit 430 may be implemented similarly to the circuit 230 in FIG. 5. The circuit 430 may be omitted depending upon the particular implementation of the circuit 432. When the circuit 430 is not implemented, the signal DK may be presented directly to the circuit 432.

The circuit 430 may have an input that may receive the signal DK and an output that may present a signal (e.g., C) to an input of the circuit 432. The circuit 432 may have an output that may present a signal (e.g., BLWC(t)) to an input of the circuit 434 and a first input of the circuit 436. The signal BLWC(t) may comprise low frequency content to be restored to the received signal. The circuit 434 may have an output that may present a signal (e.g., BLWCK) to a first input of the circuit 438. The circuit 438 may have a second input that may receive the signal EK and an output that may present a signal (e.g., G) to a second input of the circuit 436. The signal G may comprise a loop gain value to be applied to the low frequency content to be restored. The circuit 434 generally converts the signal BLWC(t) from the analog domain to the digital domain. The circuit 438 generally provides an adaptation loop for determining the appropriate gain value. In one example, the circuit 438 may implement loop gain adaptation using a least means squared (LMS) technique. The circuit 436 may have an output that may present the signal FBK(t). The signal FBK(t) generally comprises a product of the signal BLWC(t) and the signal G.

Figure 7:
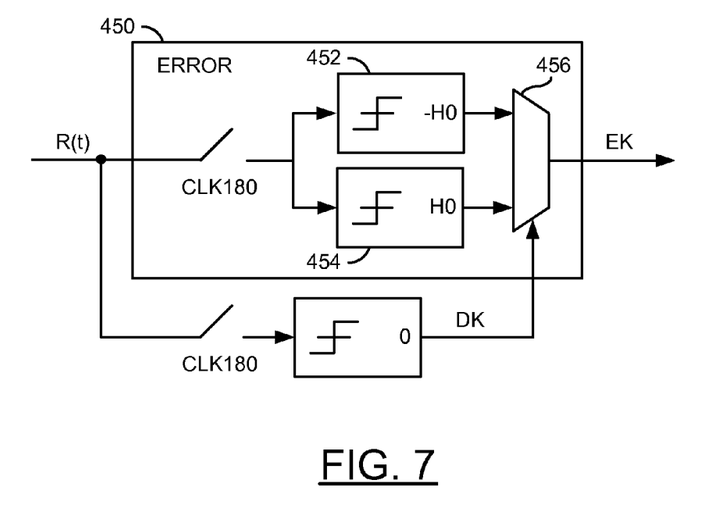
FIG. 7 is a block diagram illustrating an example circuit for implementing an error signal generator of FIGS. 4 and 6.

Referring to FIG. 7, a diagram of a circuit 450 is shown illustrating an example error signal generator in accordance with an example embodiment of the present invention. The circuit 450 may be used to implement the circuit 218 of FIG. 4 and the circuit 418 of FIG. 6. In one example, the circuit 450 may comprise a block (or circuit) 452, a block (or circuit) 454 and a block (or circuit) 456. The circuit 452 may be implemented, in one example, as a capture latch with a threshold of −H0. The circuit 454 may be implemented, in one example, as a capture latch with a threshold of H0. H0 generally represents a target level of a receiver in which the circuit 450 is implemented. The circuit 456 may be implemented, in one example, as a multiplexer.

The signal R(t) may be presented to an input of the circuit 452 and an input of the circuit 454. For example, the signal R(t) may be sampled in response to a sampling clock (e.g., CLK180) and the samples presented to the circuit 452, the circuit 454, and a data detector associated with the circuit 450. An output of the circuit 452 may be presented to a first input of the circuit 456. An output of the circuit 454 may be presented to a second input of the circuit 456. The signal DK may be presented to a third input (e.g., a control input) of the circuit 456. The circuit 456 may have an output that may present the signal EK. The sign of the signal EK may be obtained by using the two error latches 452 and 454. One of the latches is selected based on DK since DK is not known ahead of time.

Figure 8:
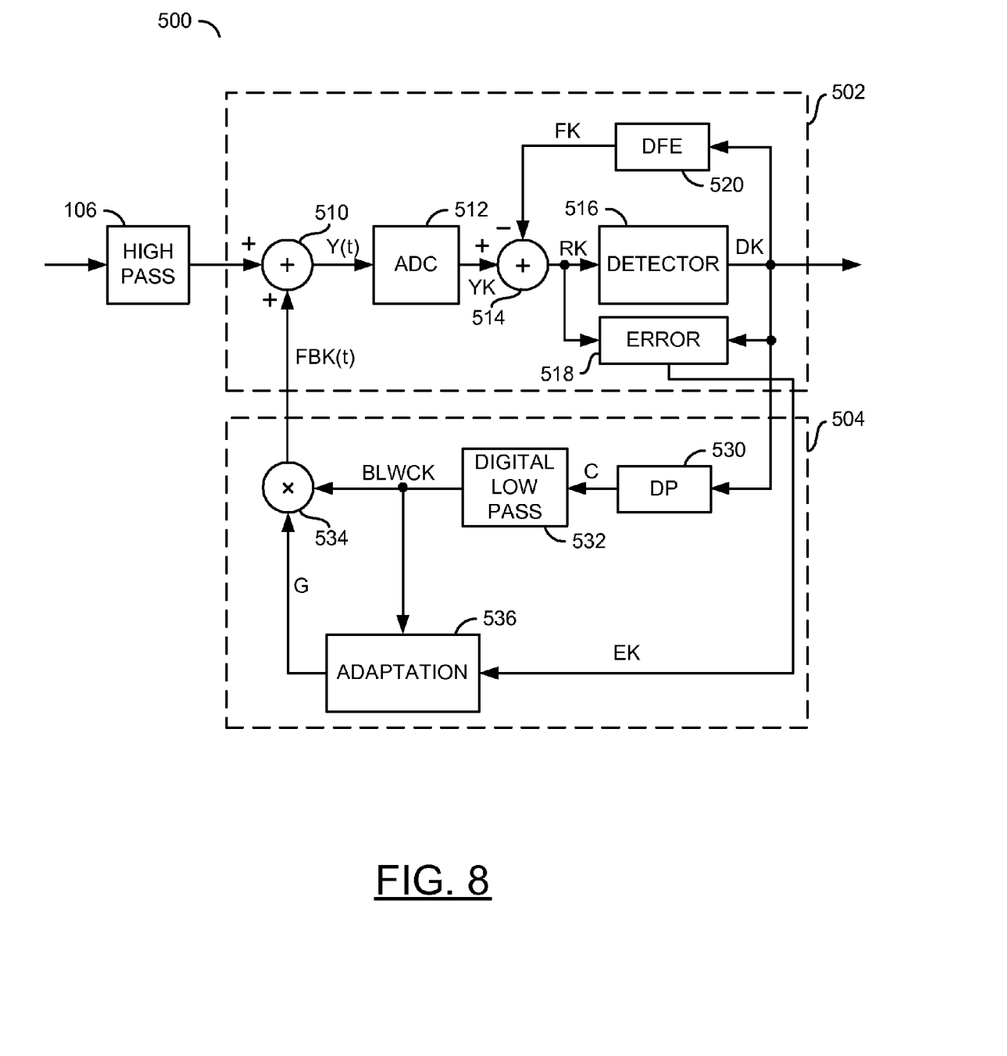
FIG. 8 is a block diagram illustrating still another example circuit implementing baseline wander correction loop gain adaptation in accordance with another example embodiment of the present invention.

Referring to FIG. 8, a block diagram of a circuit 500 is shown illustrating another example implementation of baseline wander correction loop gain adaptation in accordance with another example embodiment of the present invention. In one example, the circuit 500 may comprise a block (or circuit) 502 and a block or circuit 504. The circuit 502 may be implemented, in one example, as a data recovery circuit. The circuit 504 may be implemented, in one example, as a baseline wander correction circuit. The circuit 502 may have a first input that may receive the signal from the coupling 106, a second input that may receive a signal (e.g., FBK(t)), a first output that may present a signal (e.g., DK), and a second output that may present a signal (e.g., EK). The signal DK may comprise recovered data. The signal EK may comprise an error signal. The signal FBK(t) may comprise low frequency content to be restored to the received signal from the coupling 106. The circuit 504 may have a first input that may receive the signal DK, a second input that may receive the signal EK, and an output that may present the signal FBK(t).

The circuit 502 may comprise a block (or circuit) 510, a block (or circuit) 512, a block (or circuit) 514, a block (or circuit) 516, a block (or circuit) 518, and a block (or circuit) 520. The circuit 510 may be implemented, in one example, as an adder. The circuit 512 may be implemented, in one example, as an analog to digital converter (ADC). The circuit 514 may be implemented, in one example, as an adder. The circuit 516 may be implemented, in one example, as a symbol detector, slicer, or other data detection circuit. The circuit 518 may be implemented, in one example, as an error signal generator. The circuit 520 may implement a decision feedback equalizer (DFE). The circuits 510-520 may be implemented using conventional techniques.

The circuit 510 may have a first input that may receive the signal from the coupling 106, a second input that may receive the signal FBK(t), and an output that may present a signal (e.g., (Y(t)). The signal Y(t) may comprise a sum of the signal from the coupling 106 and the signal FBK(t). The signal Y(t) may be presented to an input of the circuit 512. The circuit 512 may have an output that may present a digital signal (e.g., YK) to a first input of the circuit 514. The circuit 514 may have a second input that may receive a signal (e.g., FK) and an output that may present a signal (e.g., RK). The signal RK may comprise a difference between the output of the circuit 512 and the signal FK. The circuit 516 may have an input that may receive the signal RK and an output presenting the signal DK. The circuit 518 may have a first input that may receive the signal RK, a second input that may receive the signal DK, and an output that may present a signal (e.g., EK). The signal EK may implement an error signal. The circuit 520 may have an input that may receive the signal DK and an output that may present the signal FK. In one example, the circuit 520 may also receive the signal EK.

The circuit 504 may comprise a block (or circuit) 530, a block (or circuit) 532, a block (or circuit) 534, and a block (or circuit) 536. The circuit 530 may implement an optional data processing (DP) circuit. The circuit 532 may be implemented, in one example, as an digital low pass filter. The circuit 534 may be implemented, in one example, as a multiplier. The circuit 536 may implement a gain adaptation loop in accordance with an embodiment of the present invention. The circuit 530, when implemented, generally processes the signal DK for use in controlling the circuit 532. The circuit 530 may be implemented similarly to the circuit 230 in FIG. 5. The circuit 530 may be omitted depending upon the particular implementation of the circuit 532. When the circuit 530 is not implemented, the signal DK may be presented directly to the circuit 532.

The circuit 530 may have an input that may receive the signal DK and an output that may present a signal (e.g., C) to an input of the circuit 532. The circuit 532 may have an output that may present a signal (e.g., BLWCK) to a first input of the circuit 534 and a first input of the circuit 536. The signal BLWCK may comprise low frequency content to be restored to the received signal. The circuit 536 may have a second input that may receive the signal EK and an output that may present a signal (e.g., G) to a second input of the circuit 534. The signal G may comprise a loop gain value to be applied to the low frequency content to be restored. The circuit 536 generally provides an adaptation loop for determining an appropriate gain value. In one example, the circuit 536 may use a least means squared (LMS) technique for adapting the loop gain. The circuit 534 may have an output that may present the signal FBK(t). The signal FBK(t) generally comprises a product of the signal BLWCK and the signal G.

Figure 9:
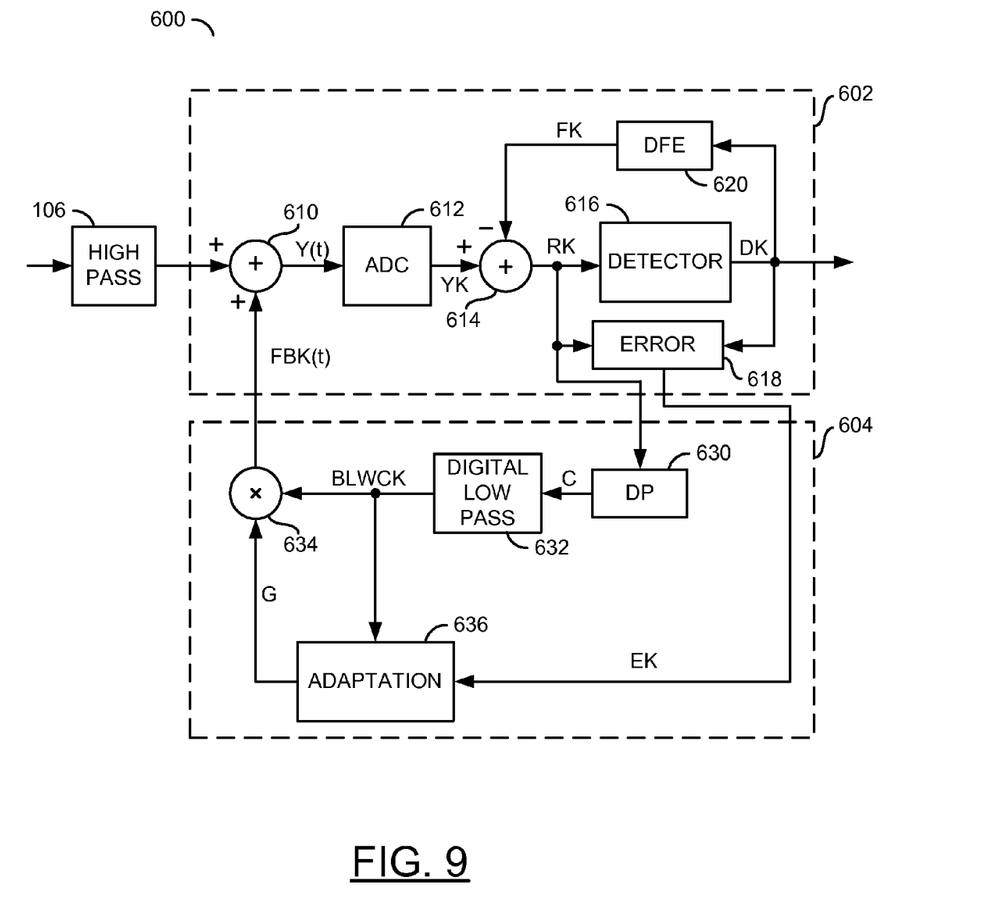
FIG. 9 is a block diagram illustrating yet another example circuit implementing baseline wander correction loop gain adaptation in accordance with another example embodiment of the present invention.

Referring to FIG. 9, a block diagram of a circuit 600 is shown illustrating another example implementation of baseline wander correction loop gain adaptation in accordance with another example embodiment of the present invention. In one example, the circuit 600 may comprise a block (or circuit) 602 and a block or circuit 604. The circuit 602 may be implemented, in one example, as a data recovery circuit. The circuit 604 may be implemented, in one example, as a baseline wander correction circuit. The circuit 602 may have a first input that may receive the signal from the coupling 106, a second input that may receive a signal (e.g., FBK(t)), a first output that may present a signal (e.g., RK), a second output that may present a signal (e.g., DK), and a third output that may present a signal (e.g., EK). The signal RK may comprise a sampled received signal. The signal DK may comprise recovered data (e.g., symbols, bits, etc). The signal EK may comprise an error signal. The signal FBK(t) may comprise low frequency content to be restored to the received signal from the coupling 106. The circuit 604 may have a first input that may receive the signal RK, a second input that may receive the signal EK, and an output that may present the signal FBK(t).

The circuit 602 may comprise a block (or circuit) 610, a block (or circuit) 612, a block (or circuit) 614, a block (or circuit) 616, a block (or circuit) 618, and a block (or circuit) 620. The circuit 610 may be implemented, in one example, as an adder. The circuit 612 may be implemented, in one example, as an analog to digital converter (ADC). The circuit 614 may be implemented, in one example, as an adder. The circuit 616 may be implemented, in one example, as a symbol detector, slicer, or other data detection circuit. The circuit 618 may be implemented, in one example, as an error signal generator. The circuit 620 may implement a decision feedback equalizer (DFE). The circuits 610-620 may be implemented using conventional techniques.

The circuit 610 may have a first input that may receive the signal from the coupling 106, a second input that may receive the signal FBK(t), and an output that may present a signal (e.g., (Y(t)). The signal Y(t) may comprise a sum of the signal from the coupling 106 and the signal FBK(t). The signal Y(t) may be presented to an input of the circuit 612. The circuit 612 may have an output that may present a digital signal (e.g., YK) to a first input of the circuit 614. The circuit 614 may have a second input that may receive a signal (e.g., FK) and an output that may present a signal (e.g., RK). The signal RK may comprise a difference between the signal YK and the signal FK. The circuit 616 may have an input that may receive the signal RK and an output presenting the signal DK. The circuit 618 may have a first input that may receive the signal RK, a second input that may receive the signal DK, and an output that may present the signal EK. The circuit 620 may have an input that may receive the signal DK and an output that may present the signal FK. In one example, the circuit 620 may also receive the signal EK.

The circuit 604 may comprise a block (or circuit) 630, a block (or circuit) 632, a block (or circuit) 634, and a block (or circuit) 636. The circuit 630 may implement an optional data processing (DP) circuit. The circuit 632 may be implemented, in one example, as an digital low pass filter. The circuit 634 may be implemented, in one example, as a multiplier. The circuit 636 may implement a gain adaptation loop in accordance with an embodiment of the present invention. The circuit 630, when implemented, generally processes the signal RK for use in controlling the circuit 632. In one example, the circuit 630 may be implemented similarly to the circuit 230 in FIG. 5. The circuit 630 may be omitted depending upon the particular implementation of the circuit 632. When the circuit 630 is not implemented, the signal RK may be presented directly to the circuit 632.

The circuit 630 may have an input that may receive the signal RK and an output that may present a signal (e.g., C) to an input of the circuit 632. The circuit 632 may have an output that may present a signal (e.g., BLWCK) to a first input of the circuit 634 and a first input of the circuit 636. The signal BLWCK may comprise low frequency content to be restored to the received signal. The circuit 636 may have a second input that may receive the signal EK and an output that may present a signal (e.g., G) to a second input of the circuit 634. The signal G may comprise a loop gain value to be applied to the low frequency content to be restored. The circuit 636 generally provides an adaptation loop for determining an appropriate gain value. The circuit 634 may have an output that may present the signal FBK(t). The signal FBK(t) generally comprises a product of the signal BLWCK and the signal G.

Figure 10:
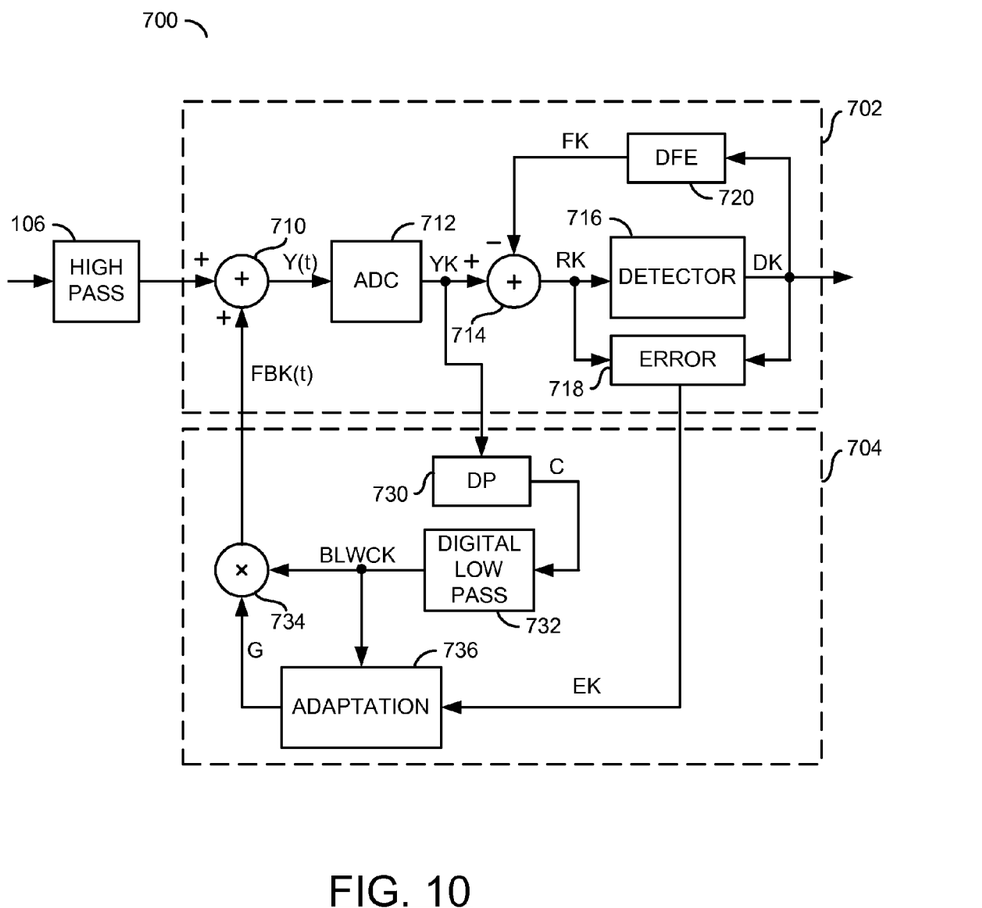
FIG. 10 is a block diagram illustrating still another example circuit implementing baseline wander correction loop gain adaptation in accordance with another example embodiment of the present invention.

Referring to FIG. 10, a block diagram of a circuit 700 is shown illustrating another example implementation of baseline wander correction loop gain adaptation in accordance with another example embodiment of the present invention. In one example, the circuit 700 may comprise a block (or circuit) 702 and a block or circuit 704. The circuit 702 may be implemented, in one example, as a data recovery circuit. The circuit 704 may be implemented, in one example, as a baseline wander correction circuit. The circuit 702 may have a first input that may receive the signal from the coupling 106, a second input that may receive a signal (e.g., FBK(t)), a first output that may present a signal (e.g., YK), a second output that may present a signal (e.g., DK), and a third output that may present a signal (e.g., EK). The signal YK may comprise a digitized version of a received signal (e.g., Y(t)). The signal DK may comprise recovered data (e.g., symbols, bits, etc). The signal EK may comprise an error signal. The signal FBK(t) may comprise low frequency content to be restored to the received signal from the coupling 106. The circuit 704 may have a first input that may receive the signal YK, a second input that may receive the signal EK, and an output that may present the signal FBK(t).

The circuit 702 may comprise a block (or circuit) 710, a block (or circuit) 712, a block (or circuit) 714, a block (or circuit) 716, a block (or circuit) 718, and a block (or circuit) 720. The circuit 710 may be implemented, in one example, as an adder. The circuit 712 may be implemented, in one example, as an analog to digital converter (ADC). The circuit 714 may be implemented, in one example, as an adder. The circuit 716 may be implemented, in one example, as a symbol detector, slicer, or other data detection circuit. The circuit 718 may be implemented, in one example, as an error signal generator. The circuit 720 may implement a decision feedback equalizer (DFE). The circuits 710-720 may be implemented using conventional techniques.

The circuit 710 may have a first input that may receive the signal from the coupling 106, a second input that may receive the signal FBK(t), and an output that may present the signal Y(t) to an input of the circuit 712. The signal Y(t) may comprise a sum of the signal from the coupling 106 and the signal FBK(t). The circuit 712 may have an output that may present the signal YK to a first input of the circuit 714. The circuit 714 may have a second input that may receive a signal (e.g., FK) and an output that may present a signal (e.g., RK). The signal RK may comprise a difference between the signal YK and the signal FK. The circuit 716 may have an input that may receive the signal RK and an output presenting the signal DK. The circuit 718 may have a first input that may receive the signal RK, a second input that may receive the signal DK, and an output that may present the signal EK. The circuit 720 may have an input that may receive the signal DK and an output that may present the signal FK. In one example, the circuit 720 may also receive the signal EK.

The circuit 704 may comprise a block (or circuit) 730, a block (or circuit) 732, a block (or circuit) 734, and a block (or circuit) 736. The circuit 730 may implement an optional data processing (DP) circuit. The circuit 732 may be implemented, in one example, as an digital low pass filter. The circuit 734 may be implemented, in one example, as a multiplier. The circuit 736 may implement a gain adaptation loop. The circuit 730, when implemented, generally processes the signal YK for use in controlling the circuit 732. In one example, the circuit 730 may be implemented similarly to the circuit 230 in FIG. 5. The circuit 730 may be omitted depending upon the particular implementation of the circuit 732. When the circuit 730 is not implemented, the signal YK may be presented directly to the circuit 732.

The circuit 730 may have an input that may receive the signal YK and an output that may present a signal (e.g., C) to an input of the circuit 732. The circuit 732 may have an output that may present a signal (e.g., BLWCK) to a first input of the circuit 734 and a first input of the circuit 736. The signal BLWCK may comprise a baseline wander correction signal. In one example, the signal BLWCK may comprise low frequency content to be restored to the received signal. The circuit 736 may have a second input that may receive the signal EK and an output that may present a signal (e.g., G) to a second input of the circuit 734. The signal G may comprise a loop gain value to be applied to the low frequency content to be restored. The circuit 736 generally provides an adaptation loop for determining an appropriate gain value. In one example, the circuit 736 may implement the adaptation loop using a least means squared technique. The circuit 734 may have an output that may present the signal FBK(t). The signal FBK(t) generally comprises a product of the signal BLWCK and the signal G.

Figure 11:
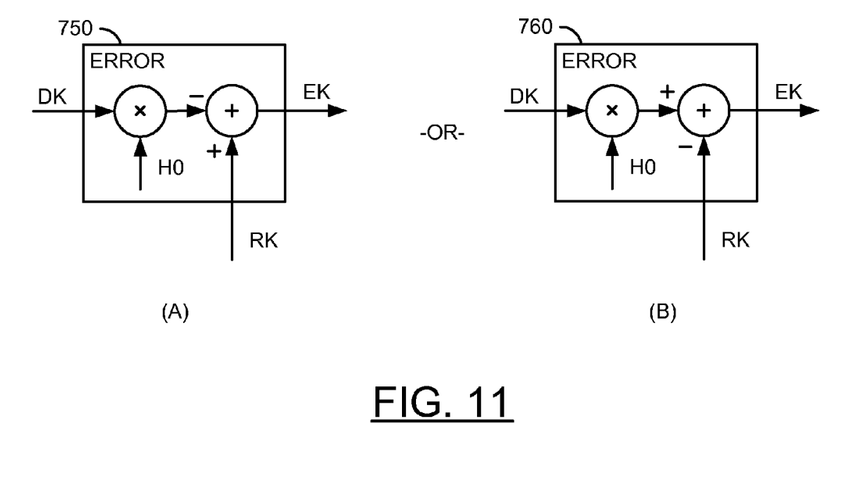
FIG. 11 is a block diagram illustrating example circuits for implementing an error signal generator of FIGS. 8-10.

Referring to FIG. 11, a diagram is shown illustrating example implementations of a circuit 750 and a circuit 760. The circuits 750 and 760 may implement error signal generating circuits. In one example, one of the circuits 750 and 760 may be used to implement the circuits 518, 618, and 718 (described above in connection with FIGS. 8-10, respectively).

The signal RK may be expressed, in one example, by the following equation:

RK=(YK+G*BLWCK)−H1*DK(−1)−H2*DK(−2)− . . . −HM*DK(−M), where M is the number of taps in the DFE 520, 620, or 720. Adaptation of the gain G may be based upon the error signal EK. The error signal EK may be expressed by one of the following equations:

$EK=H0*DK-RK;$ $EK=RK-H0*DK.$

In one example, the circuit 750 may implement the signal EK=RK−H0*DK. In another example, the circuit 760 may implement the signal EK=H0*DK−RK. The second derivative of EK with respect to G, may be expressed:

$dEK^2/dG=-EK*BLWCK.$

The gradient of the BLWC gain adaptation may be expressed by the following expression:

$$-\text{sgn}(EK)*\text{sgn}(BLWCK).$$

The adaptation blocks disclosed herein are generally implemented based upon the above gradient to adjust the respective gains.

Figure 12:
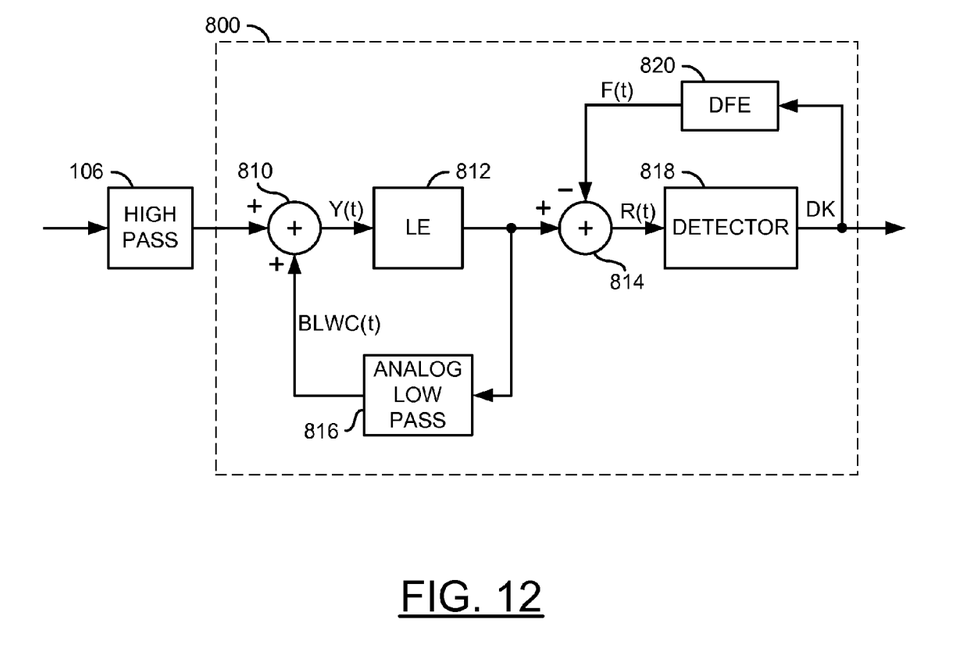
FIG. 12 is a block diagram illustrating yet one more example circuit implementing a baseline wander correction in accordance with yet another example embodiment of the present invention.

Referring to FIG. 12, a block diagram of a circuit 800 is shown illustrating yet one more example implementation of a baseline wander correction in accordance with yet another example embodiment of the present invention. In one example, the circuit 800 may comprise a block (or circuit) 810, a block (or circuit) 812, a block (or circuit) 814, a block (or circuit) 816, a block (or circuit) 818, and a block (or circuit) 820. The circuit 810 may be implemented, in one example, as an adder. The circuit 812 may be implemented, in one example, as a linear equalizer (LE). The circuit 814 may be implemented, in one example, as an adder. The circuit 816 may be implemented, in one example, as an analog low pass filter. The circuit 818 may be implemented, in one example, as a symbol detector, slicer, or other data detection circuit. The circuit 820 may implement a decision feedback equalizer (DFE).

The circuit 810 may have a first input that may receive the signal from the coupling 106, a second input that may receive the signal BLWC(t), and an output that may present the signal Y(t) to an input of the circuit 812. The signal Y(t) may comprise a sum of the signal from the coupling 106 and the signal BLWC(t). The circuit 812 may have an output that may present a signal to a first input of the circuit 814 and an input of the circuit 816. The circuit 814 may have a second input that may receive a signal (e.g., F(t)) and an output that may present a signal (e.g., R(t)). The signal R(t) may comprise a difference between the output of the LE 812 and the signal F(t). The circuit 816 may have an input that may receive the signal from the output of the circuit 812. The circuit 818 may have an input that may receive the signal R(t) and an output that may present a signal (e.g., DK). The circuit 820 may have an input that may receive the signal DK and an output that may present the signal F(t).

Figure 13:
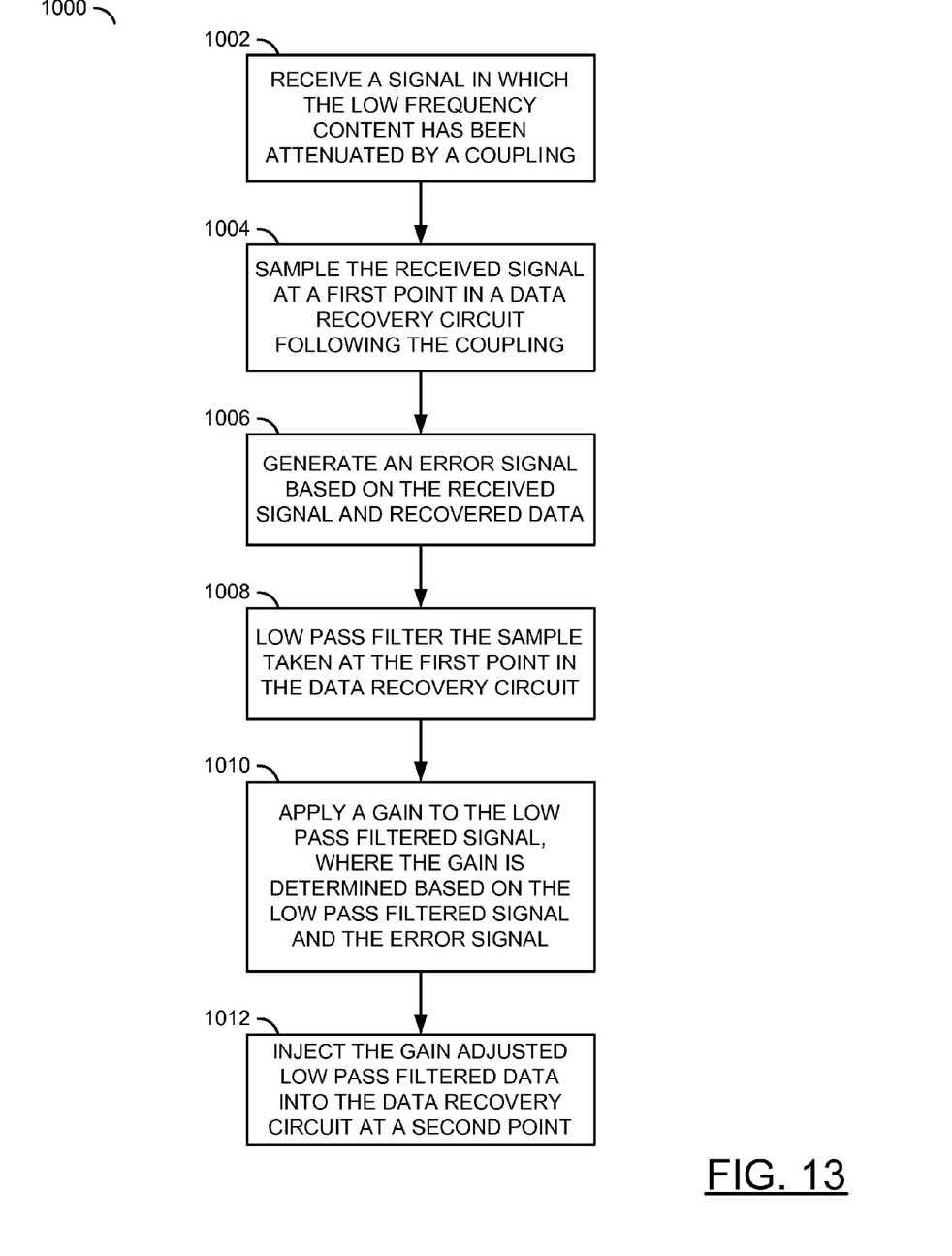
FIG. 13 is a flow diagram illustrating a process for correcting baseline wander in accordance with example embodiments of the present invention.

Referring to FIG. 13, a flow diagram is shown illustrating a process (or method) 1000 for correcting baseline wander in accordance with example embodiments of the present invention. The method 1000 may comprise a step (or state) 1002, a step (or state) 1004, a step (or state) 1006, a step (or state) 1008, a step (or state) 1010, a step (or state) 1012. In the step 1002, the process 1000 may begin by receiving a signal in which the low frequency content is attenuated, for example, due to high pass filtering by a medium carrying the signal and a coupling (e.g., a capacitive coupling, an inductive coupling, a poor electrical contact, etc.). In the step 1004, the process 1000 may take a sample of the received signal, either in the analog domain or the digital domain, at a predefined point in a data recovery pathway after the coupling. In the step 1006, the process 1000 may generate an error signal based upon a detector input (e.g., the received signal) and a detector output (e.g., recovered data). In the step 1008, the process 1000 may low pass filter the signal taken at the predefined point of the signal pathway. In the step 1010, the process 1000 may apply a gain to the low pass filtered signal. The applied gain may be automatically determined based upon the low pass filtered signal (or an equivalent) and the error signal. In the step 1012, the process 1000 may inject the filtered signal with the applied gain into a second predefined point the data recovery pathway after the coupling.

The gain of the low pass filter may be automatically set based upon the filtered signal and the error signal. In one example, adaptation of the gain may be performed using a least mean squares (LMS) or a sign-sign least mean squares technique. In another example, the gain may be automatically adapted based upon channel loss and changes in transmitter de-emphasis setting. The gain adaption may set the gain automatically to minimize the mean squared error (MSE) at the input of the detector. The gain adaption may use the actual filtered signal from a primary low pass filter path or a representative signal generated by a parallel low pass filter path having an equivalent frequency response to the primary low pass filter path. In one example, the actual filtered signal may be sampled using a latch or analog-to-digital converter (ADC) and the sample used in the adaptation loop.

The functions performed by the diagram of FIG. 13 may be implemented using one or more of a conventional general purpose processor, digital computer, microprocessor, microcontroller, RISC (reduced instruction set computer) processor, CISC (complex instruction set computer) processor, SIMD (single instruction multiple data) processor, signal processor, central processing unit (CPU), arithmetic logic unit (ALU), video digital signal processor (VDSP) and/or similar computational machines, programmed according to the teachings of the present specification, as will be apparent to those skilled in the relevant art(s). Appropriate software, firmware, coding, routines, instructions, opcodes, microcode, and/or program modules may readily be prepared by skilled programmers based on the teachings of the present disclosure, as will also be apparent to those skilled in the relevant art(s). The software is generally executed from a medium or several media by one or more of the processors of the machine implementation.

The present invention may also be implemented by the preparation of ASICs (application specific integrated circuits), Platform ASICs, FPGAs (field programmable gate arrays), PLDs (programmable logic devices), CPLDs (complex programmable logic device), sea-of-gates, RFICs (radio frequency integrated circuits), ASSPs (application specific standard products), monolithic integrated circuits, one or more chips or die arranged as flip-chip modules and/or multi-chip modules or by interconnecting an appropriate network of conventional component circuits, as is described herein, modifications of which will be readily apparent to those skilled in the art(s).

The present invention thus may also include a computer product which may be a storage medium or media and/or a transmission medium or media including instructions which may be used to program a machine to perform one or more processes or methods in accordance with the present invention. Execution of instructions contained in the computer product by the machine, along with operations of surrounding circuitry, may transform input data into one or more files on the storage medium and/or one or more output signals representative of a physical object or substance, such as an audio and/or visual depiction. The storage medium may include, but is not limited to, any type of disk including floppy disk, hard drive, magnetic disk, optical disk, CD-ROM, DVD and magneto-optical disks and circuits such as ROMs (read-only memories), RAMS (random access memories), EPROMs (electronically programmable ROMs), EEPROMs (electronically erasable ROMs), UVPROM (ultra-violet erasable ROMs), Flash memory, magnetic cards, optical cards, and/or any type of media suitable for storing electronic instructions.

The elements of the invention may form part or all of one or more devices, units, components, systems, machines and/or apparatuses. The devices may include, but are not limited to, servers, workstations, storage array controllers, storage systems, personal computers, laptop computers, notebook computers, palm computers, personal digital assistants, portable electronic devices, battery powered devices, set-top boxes, encoders, decoders, transcoders, compressors, decompressors, pre-processors, post-processors, transmitters, receivers, transceivers, cipher circuits, cellular telephones, digital cameras, positioning and/or navigation systems, medical equipment, heads-up displays, wireless devices, audio recording, storage and/or playback devices, video recording, storage and/or playback devices, game platforms, peripherals and/or multi-chip modules. Those skilled in the relevant art(s) would understand that the elements of the invention may be implemented in other types of devices to meet the criteria of a particular application.

While the invention has been particularly shown and described with reference to the preferred embodiments thereof, it will be understood by those skilled in the art that various changes in form and details may be made without departing from the scope of the invention.

The invention claimed is:

1. An apparatus comprising:
a first circuit configured to receive a signal, wherein low frequency content of said signal is attenuated due to high pass filtering by a medium carrying said signal and a coupling; and
a second circuit configured to automatically set a gain of a baseline wander correction loop to restore said low frequency content in said signal based upon a sample taken from a first point in a signal pathway of said first circuit, wherein
said low frequency content in said signal is restored by adding a feedback signal generated by said second circuit to a second point in the signal pathway of said first circuit,
said second circuit comprises (i) a first low pass filter, (ii) a second low pass filter, (iii) a multiplier, and (iv) a gain adaptation circuit,
said first low pass filter and said second low pass filter are configured to generate a first baseline wander correction signal and a second baseline wander correction signal respectively, in response to said sample taken from said first point in said signal pathway of said first circuit,
said multiplier is configured to generate said feedback signal by scaling said second baseline wander correction signal based upon said gain of said baseline wander correction loop, and
said gain adaptation circuit is configured to set said gain of said baseline wander correction loop in response to said first baseline wander correction signal and an error signal.

2. The apparatus according to claim 1, wherein said coupling comprises at least one of an AC coupling capacitor and a transformer.

3. The apparatus according to claim 1, wherein said first circuit comprises a receiver circuit, said signal pathway comprises a receiver chain of said receiver circuit, and said second circuit comprises a baseline wander correction circuit.

4. The apparatus according to claim wherein the first point in the signal pathway of said first circuit from which said sample is taken comprises one of an output of a detector, an input of said detector, an output of a slicer, an input of said slicer, an output of an equalizer, an input of said equalizer, and an input of a summing node of said receiver.

5. The apparatus according to claim 4, wherein said equalizer comprises at least one of a linear equalizer and a decision feedback equalizer.

6. The apparatus according to claim 1, wherein said first low pass filter comprises at least one of an analog low pass filter and a digital low pass filter.

7. The apparatus according to claim 1, wherein:
said first low pass filter comprises an analog low pass filter;
said first baseline wander correction signal generated by said analog low pass filter is presented to either a latch or an analog-to-digital converter; and
said gain of said baseline wander correction loop is adapted based upon an output of said latch or said analog-to-digital converter and said error signal.

8. An apparatus comprising:
a first circuit configured to receive a signal, wherein low frequency content of said signal is attenuated due to high pass filtering by a medium carrying said signal and a coupling; and
a second circuit configured to automatically set a gain of a baseline wander correction loop to restore said low frequency content in said signal based upon a sample taken from a first point in a signal pathway of said first circuit, wherein said second circuit comprises a first low pass filter and a second low pass filter configured to generate a first baseline wander correction signal and a second baseline wander correction signal, respectively, and a gain of the first baseline wander correction signal is automatically adapted based upon an error signal and the second baseline wander correction signal.

9. The apparatus according to claim 8, wherein said second low pass filter is configured to match a transfer function of said first low pass filter.

10. The apparatus according to claim 8, wherein adaptation of said gain implements at least one of least mean squares and sign-sign least mean squares.

11. The apparatus according to claim 8, wherein said second low pass filter comprises a digital low pass filter.

12. The apparatus according to claim 1, wherein said second circuit further comprises a data processing circuit configured to control said low pass filter based upon said sample taken from said first point in said signal pathway of said first circuit.

13. The apparatus according to claim 1, wherein said apparatus is fabricated in an integrated circuit.

14. A method of correcting baseline wander comprising:
receiving a signal, wherein low frequency content of said signal is attenuated due to high pass filtering by a medium carrying said signal and a coupling method for communicating said signal to a receiver; and
automatically setting a gain of a baseline wander correction loop to restore said low frequency content in said signal based upon a sample taken from a first point in a signal pathway of said receiver after the coupling, wherein automatically setting said gain comprises (i) generating a first baseline wander correction signal and a second baseline wander correction signal in response to said sample taken from said first point in said signal pathway of said receiver using a first low pass filter and a second low pass filter, respectively, and (ii) setting a gain of said first baseline wander correction signal based upon said second baseline wander correction signal and an error signal using a gain adaptation loop.

15. The method according to claim 14, wherein correcting said baseline wander comprises low pass filtering said signal taken from said first point in said signal pathway.

16. The method according to claim 14, further comprising:
generating a product of a gain value and an output of said first low pass filter configured to filter said signal taken from said first point in said signal pathway; and adding said product to said signal at a second point in said signal pathway after said coupling.

17. The method according to claim 14, wherein said gain for said first low pass filter is automatically adapted based on channel loss and changes in transmitter de-emphasis setting.

18. The method according to claim 16, wherein the gain value is set based upon a detector error signal and a digital representation of said first baseline wander correction signal.

* * * * *